(12) United States Patent
Vincent

(10) Patent No.: US 9,220,752 B2
(45) Date of Patent: Dec. 29, 2015

(54) DIETARY PRODUCT INTENDED TO REDUCE VISCERAL FAT DURING THE PRE-OPERATIVE PHASE PRIOR TO BARIATRIC SURGERY

(71) Applicant: INTERNATIONAL NUTRITION RESEARCH COMPANY, Luxembourg (LU)

(72) Inventor: Claude Vincent, Bordeaux (FR)

(73) Assignee: INTERNATIONAL NUTRITION RESEARCH COMPANY, Luxembourg (LU)

( * ) Notice: Subject to any disclaimer, the term of this patent is extended or adjusted under 35 U.S.C. 154(b) by 0 days.

(21) Appl. No.: 14/353,605

(22) PCT Filed: Oct. 25, 2012

(86) PCT No.: PCT/EP2012/071114
§ 371 (c)(1),
(2) Date: Apr. 23, 2014

(87) PCT Pub. No.: WO2013/060759
PCT Pub. Date: May 2, 2013

(65) Prior Publication Data
US 2014/0308369 A1    Oct. 16, 2014

(30) Foreign Application Priority Data
Oct. 25, 2011   (FR) ...................................... 11 59664

(51) Int. Cl.
| | | |
|---|---|---|
| A61K 47/00 | (2006.01) |
| A61K 38/17 | (2006.01) |
| A23L 1/305 | (2006.01) |
| A23L 2/66 | (2006.01) |
| A61K 31/185 | (2006.01) |
| A61K 31/198 | (2006.01) |
| A61K 31/202 | (2006.01) |
| A61K 31/355 | (2006.01) |
| A61K 31/405 | (2006.01) |
| A61K 31/519 | (2006.01) |
| A61K 31/59 | (2006.01) |
| A61K 31/675 | (2006.01) |
| A61K 33/06 | (2006.01) |
| A61K 33/24 | (2006.01) |
| A61K 33/30 | (2006.01) |
| A61K 38/01 | (2006.01) |

(52) U.S. Cl.
CPC ........... *A61K 38/1709* (2013.01); *A23L 1/3053* (2013.01); *A23L 1/3056* (2013.01); *A23L 2/66* (2013.01); *A61K 31/185* (2013.01); *A61K 31/198* (2013.01); *A61K 31/202* (2013.01); *A61K 31/355* (2013.01); *A61K 31/405* (2013.01); *A61K 31/519* (2013.01); *A61K 31/59* (2013.01); *A61K 31/675* (2013.01); *A61K 33/06* (2013.01); *A61K 33/24* (2013.01); *A61K 33/30* (2013.01); *A61K 38/011* (2013.01); *A23V 2002/00* (2013.01)

(58) Field of Classification Search
None
See application file for complete search history.

(56) References Cited

U.S. PATENT DOCUMENTS

2004/0192615 A1* 9/2004 Hageman ..................... 514/23
2009/0181145 A1    7/2009 Pandey et al.

FOREIGN PATENT DOCUMENTS

| EP | 2 149 369 A1 | 2/2010 |
|---|---|---|
| FR | 2 902 607 A1 | 12/2007 |
| WO | 2004/014152 A1 | 2/2004 |
| WO | 2007/022312 A2 | 2/2007 |
| WO | 2009/115331 A2 | 9/2009 |
| WO | 2010/043415 A2 | 4/2010 |
| WO | 2010/047581 A1 | 4/2010 |
| WO | 2010/114627 A1 | 10/2010 |

OTHER PUBLICATIONS

Lourenco Da Costa et al.: "Effect of heat and enzymatic treatment on the antihypertensive activity of whey protein hydrolysates", International Dairy Journal, Elsevier Applied Science, Barking, GB, vol. 17, No. 6, Feb. 20, 2007, pp. 632-640, XP005895471, ISSN: 0958-6946, DOI: 10.1016/J.IDAIRYJ.2006.09.003 the whole document.
International Search Report, dated Jan. 21, 2013, from corresponding PCT application.

* cited by examiner

*Primary Examiner* — Susan Tran
(74) *Attorney, Agent, or Firm* — Young & Thompson

(57) ABSTRACT

An orally administered dietary product intended to reduce an obese person's visceral fat during the pre-operative phase prior to bariatric surgery, the product includes in particular a mixture of: a whey hydrolysate having a molecular weight of between 200 and 10,000 daltons, an isolate and/or a concentrate of whey, and calcium caseinate.

15 Claims, No Drawings

DIETARY PRODUCT INTENDED TO REDUCE VISCERAL FAT DURING THE PRE-OPERATIVE PHASE PRIOR TO BARIATRIC SURGERY

FIELD OF THE INVENTION

This invention relates to a dietary product and its use in particular for reducing visceral fat in obese patients during the pre-operative phase of a bariatric surgical intervention.

BACKGROUND OF THE INVENTION

The number of obese individuals, more particularly in developed countries, continues to grow.

The risks brought about by obesity are numerous. In particular, it is known that obesity increases cardiometabolic risk, which refers to the presence in an individual of several clinical and biological signs that increase the risk of heart disease, cardiovascular accidents, and type 2 diabetes.

In the case of morbid and severe obesity, it may be necessary to resort to bariatric surgery, which makes it possible to restrict the absorption of food, in particular by reducing the gastric capacity, thus reducing the daily caloric supply, or by causing a malabsorption.

There are several types of bariatric surgery interventions, such as the insertion of a ring, sleeve, biliopancreatic diversion, or bypass. All of these techniques, which are applied by incision of the abdominal wall for laparoscopic surgery, are difficult to implement, because the presence of visceral body fat around the liver and liver steatosis hamper the surgeon during his intervention by limiting access to the stomach.

This is why it is essential, during a bariatric pre-operative phase, to be able to reduce visceral fat and the size of the steatosic liver because it is known that severely obese patients have non-alcoholic steatohepatitis or NASH.

The current solution consists in imposing a strict diet on the patient who will undergo the intervention. However, this diet is difficult to follow for the patient who will undergo the intervention and also brings about risks of hepatic stenosis. In addition, it is demonstrated that this kind of regimen aggravates food compulsions and the tendency toward depression by increasing the tryptophan deficiency already existing in the obese individual, caused by chronic inflammation and stress. Finally, this diet aggravates the symptomatic deficiencies of overweight individuals.

Furthermore, the obese individuals suffer from numerous deficiencies of micronutrients, in particular anti-inflammatory micronutrients such as zinc, chromium, omega-3 fatty acids, arginine, and taurine, which interfere with healing. In addition, with abdominal obesity, the patients have a high fibrogen level promoting the incidence of post-operative thrombosis.

Finally, the patient arrives in the operating room with a significant stress level that is added to his natural stress level.

All of these phenomena linked to the state of obesity of the patient will accentuate the difficulties of bariatric intervention if they are not treated, and a strict diet, at less than 800 kcal/day, before the operation will only aggravate them.

In addition, it is essential that the loss of weight before the operation is not reflected by a loss in lean body mass because after the intervention, the loss of several kilograms per week will be reflected by a significant loss of lean body mass that affects the basic metabolism and often brings about a regaining of weight. In addition, the reduction of lean body mass also affects an organ such as the heart, which can be dangerous during anesthesia and during the intervention in general.

There is therefore a need for a solution that is effective, natural, and easy to use, which is able to reduce the visceral fat specifically and to respond to deficiencies and shortcomings in obese individuals during the pre-operative phase of a bariatric surgical intervention.

SUMMARY OF THE INVENTION

To respond to this, this invention proposes using a particular composition comprising a mixture of active ingredients consisting of at least:
  A whey hydrolyzate with a molecular weight of between 200 and 10,000 daltons,
  An isolate and/or a concentrate of whey, and
  Calcium caseinate.

Advantageously, such a composition can be used as a dietary product that is intended in particular for reducing visceral fat in obese individuals during the pre-operative phase of a bariatric surgical intervention, and makes it possible to lose between 25 and 50% of the volume of the liver.

Furthermore, such a composition makes it possible to combat specific deficiencies and shortcomings in obese individuals and thus to reduce the risks of a bariatric operation.

The invention is now described in detail.

DETAILED DESCRIPTION OF THE INVENTION

The purpose of the invention is therefore a dietary composition for its use as a dietary product or for the preparation of an orally-administered dietary product for the reduction of visceral fat in an obese individual during the pre-operative phase of a bariatric surgery intervention, comprising a mixture of active ingredients that consists of at least:
  A whey hydrolyzate with a molecular weight of between 200 and 10,000 daltons,
  An isolate and/or a concentrate of whey, and
  Calcium caseinate.

In terms of the invention, dietary composition or dietary product is defined as a product that is intended for a particular diet, in addition to a restrictive regimen and/or a balanced diet. The dietary composition or the dietary product according to the invention is particularly suited to individuals who wish to prepare effectively for a bariatric operation by limiting the operative risks and by having a better recovery.

In terms of the invention, whey hydrolyzate is defined as any molecule or mixture of molecules obtained by a process that comprises a stage for chemical hydrolysis or enzymatic hydrolysis of whey.

In terms of the invention, whey isolate is defined as a whey extract that contains less than 1% lactose and fats.

In terms of the invention, whey concentrate is defined as a whey extract that is obtained by concentration of whey.

The whey hydrolyzate has a molecular weight of between 200 and 10,000 daltons, preferably between 200 and 3,500 daltons. It essentially consists of dipeptides and tripeptides.

In a preferred way, it involves a peptide hydrolyzate of whey comprising at least 90% peptides by weight of dry material of the hydrolyzate.

The isolate and/or the concentrate of whey preferably has/have a molecular weight of between 15,000 and 20,000 daltons.

The whey isolate is preferably produced from fresh milk and from dairies that do not pasteurize the milk to prevent the destruction of beta-lactoglobulin and alpha-lactalbumin and that extract the whey by ultrafiltering or microfiltering (size of the filters of 0.1 µm). The isolate that is obtained by ion exchange is less suitable because of its low content of beta-lactoglobulin and alpha-lactalbumin. The isolate contains less than 1% lactose and fats, and its peptide concentration is preferably at least 90% by weight of dry material.

The whey concentrate is preferably obtained from an unpasteurized dairy whey, containing beta-lactoglobulin, alpha-lactalbumin, and glycomacropeptides. The concentration of peptides of the concentrate is preferably at least 80% by weight of dry material.

Furthermore, the calcium caseinate used in the composition according to the invention preferably has a molecular weight of between 20,000 and 35,000 daltons.

Advantageously, the different components of the composition act in synergy. The presence of the particular hydrolyzate associated with that of the isolate and/or the concentrate of whey makes it possible in particular to accelerate the loss of visceral fat and manipulates the feeling of fullness. The calcium caseinate in particular has an appetite-suppressant effect.

In a preferred way, the ratio by weight between the calcium caseinate and the mixture consisting of the hydrolyzate and the isolate and/or the concentrate of whey is from 0.8 to 1.2 in the composition. Such a characteristic also promotes the loss of visceral fat.

According to a particularly suitable embodiment, the mixture of active ingredients of the composition also comprises a mixture of amino acids. The presence of amino acids makes it possible to improve the effectiveness of the dietary composition according to the invention.

The amino acids that are present in the composition are preferably at least tryptophan, glutamine, leucine, arginine and/or taurine, but the composition can contain other amino acids, such as isoleucine, valine, phenylalanine or tyrosine. Very preferably, the composition according to the invention comprises at least tryptophan, leucine, arginine, and taurine.

When tryptophan is present, it should represent between 6 and 9%, preferably approximately 7%, by weight of neutral amino acids that are present in the composition (leucine, isoleucine, valine, phenylalanine, tyrosine, and tryptophan). This particular proportion makes it possible to ensure that a suitable quantity of tryptophan can pass through the hematoencephalic barrier to be transformed into serotonin in such a way in particular as to affect the feeling of fullness in addition to the actions of the whey hydrolyzate, arginine, and taurine coupled to zinc for the incretin hormones, and to promote stress management.

When arginine and taurine are present, the ratio of the weight of arginine to the weight of taurine is between 1.5 and 2.

In addition to the mixture of hydrolyzate, isolate and/or concentrate of whey and calcium caseinate, and amino acids, the mixture of active ingredients of the composition according to the invention can comprise one or more of the elements that are selected from among milk calcium, magnesium, vitamin B6, vitamin B9, vitamin E, vitamin D, zinc, and chromium.

Likewise, the composition can contain essential fatty acids, in particular omega-3 fatty acids. These are preferably omega-3 fatty acids of plant origin, with a high proportion of EPA.

The different components of the composition according to the invention act in synergy for obtaining surprising effects that are particularly suitable for the reduction of visceral fat during the pre-operative phase of a bariatric surgery intervention.

According to a preferred embodiment, the mixture of active ingredients of the composition according to the invention comprises at least:
  8 to 12% whey hydrolyzate,
  15 to 20% isolate and/or concentrate of whey,
  20 to 25% calcium caseinate,
with the percentages being given by weight of dry material of all of the active ingredients that are present in the composition (apart from the possible vehicles). The composition can also contain elements that are added freely, such as amino acids, vitamins, and minerals, which are added to the native components of the whey hydrolyzate, the whey isolate, the whey concentrate, and calcium caseinate.

The composition according to the invention preferably consists of at least:
  1.5 to 3% tryptophan,
  12 to 20% branched amino acids,
  6 to 10% aromatic amino acids,
  0.8 to 1.5% taurine,
  1.6 to 3% arginine,
  1.2 to 3% milk calcium,
  0.5 to 1% magnesium,
  0.4 to 1% omega-3 fatty acids,
  1 to 2 mg of vitamin B6 per 50 g of the composition without vehicles,
  5 to 15 mg of zinc per 50 g of composition without vehicles,
  1 to 3 μg of vitamin D per 50 g of composition without vehicles,
  75 to 150 μg of chromium per 50 g of composition without vehicles,
  100 μg of vitamin B9 per 50 g of composition without vehicles,
  10 mg of vitamin E per 50 g of composition without vehicles,
with the percentages being given by weight of dry material of all of the active ingredients that are present in the composition (apart from the possible vehicles), a portion of the components coming from the whey hydrolyzate, the whey isolate, the whey concentrate, and calcium caseinate, and the remainder being freely added in the form of amino acids, vitamins, and minerals.

The branched amino acids of the composition consist of leucine, isoleucine, and valine, preferably:
  50 to 60% leucine,
  18 to 25% isoleucine, and
  20 to 28% valine,
and the aromatic amino acids of tryptophan, phenylalanine, and tyrosine, preferably:
  15 to 24% tryptophan,
  38 to 46% phenylalanine, and
  35 to 43% tyrosine.

The composition according to the invention can be obtained by a process as described below:
  A first mixture is obtained by mixing components in the following order: calcium caseinate, whey isolate, whey concentrate, whey hydrolyzate, free amino acids, magnesium, and milk calcium. The pH is to be around 7 and is stabilized at this level.
  Addition to the first mixture of vitamins, minerals, and fatty acids.
  A powder that can be transformed into a tablet or liquid, or else used in its powder form in packets, sticks, containers, or capsules, for example, is thus obtained.

The composition according to the invention, when it is administered by oral means in sufficient quantity, makes it possible to act directly on the loss of fat, in particular owing to the presence of the mixture of hydrolyzate and isolate and/or concentrate of whey.

It also acts as an appetite suppressant and ensures a feeling of fullness, in particular by the action of whey hydrolyzate. This effect is enhanced in the presence of tryptophan and can even be accentuated owing to the presence of other components, in particular milk calcium, histidine, vitamin B6, and/or magnesium, with the various components then acting in synergy.

The composition according to the invention is particularly suitable for reducing visceral fat around the liver in a patient before a bariatric surgery operation and for reducing the size of the liver, itself also loaded with fat. A particularly suitable therapy for the preparation in a bariatric surgical intervention for inserting a ring, sleeve, gastric bypass or biliopancreatic diversion is 6 weeks with a dietary restriction that is 20 to 40% below the REE (Resting Energy Expenditure), also called basic metabolism of the individual who undergoes the therapy. The reduction in visceral fat thus obtained makes it possible for the surgeon to perform his operation in the best manner possible and to reduce the intervention time by 5 to 10%.

The composition according to the invention also makes it possible to lose weight permanently in particular by the supply of tryptophan that regulates fullness in synergy with the action on the inflammation of taurine, arginine, zinc, and chromium by a regulation of the NF-kappa B signal of the macrophages of adipocytokines and regulation of incretin hormones. In addition, it reduces the circumference of the waistline, while maintaining the lean body mass, in particular by the supply of branched amino acids.

According to another advantage, the composition is also capable of affecting other factors of operative risk. In particular, it is capable of:
  Reducing stress and depression as well as normalizing arterial tension, which are factors aggravating risks of anesthesia,
  Reducing ultrasensitive CRP inflammation that makes it possible to improve healing time,
  Regulating the fibrinogen coagulation factor that makes it possible to prevent thromboses,
  Beginning to treat a possible hepatic steatosis by the loss of visceral fat associated with vitamin E,
  Combating tryptophan deficiency before the operation, where the lack of tryptophan in depressive obese patients seriously retards weight loss and is an essential factor in regaining weight after the operation.

The composition according to the invention can come in any form that is suitable for administration by oral means. It can come in particular in the form of powder or granules, ready-to-use drinks, bars or logs, with conventional vehicles and additional ingredients that are known to one skilled in the art being added to the composition.

Preferably, it comes in the form of powder or granules packaged in a packet to be diluted in water.

The daily dose of composition according to the invention (dose of a mixture of active ingredients without vehicles) is preferably between 66 and 110 g, preferably in two servings of 33 to 55 g, one taken in the morning at breakfast or at 1100 hours with a snack, and one with a snack in the afternoon.

Advantageously, the bioavailability in the body of amino acids, peptides and proteins that are present in the composition in the body is between 10 minutes and 5 hours, which makes possible an action that is both rapid and that continues over time in such a way as to limit the quantity of food to be taken daily.

In addition, the presence of milk calcium makes it possible to enhance the palatability of the dietary product according to the invention by masking in particular the bitter taste of the whey hydrolyzate in such a way that it takes part in eliminating the risk that the individuals stop consuming it for reasons of taste and abandon their regimen before its end.

The dietary composition makes it possible to reduce the visceral fat in overweight individuals, in particular by the acceleration of the lipolysis process, the regulation of the oxidation-inflammation-coagulation triad, and the supply of active ingredients compensating for the pathological deficiencies of obese individuals.

The combination of fatty acids, in particular omega-3 fatty acids, with milk calcium and the particular amino acid mixture according to the invention also makes it possible to retard the transformation of pre-adipocytes into visceral adipocytes.

The invention is now illustrated by a nonlimiting example of dietary composition, coming in the form of a powder of 55 g (active ingredients and vehicles) packaged in a packet.

This composition is obtained from the following active ingredients:
  5 g of whey hydrolyzate with a molecular weight of between 200 and 3,500 daltons,
  10 g of isolate and/or concentrate of whey with a molecular weight of between 15,000 and 20,000 daltons,
  13 g of calcium caseinate with a molecular weight of between 20,000 and 35,000 daltons,
  1 mg of vitamin B6,
  10 mg of zinc,
  0.45 g of taurine,
  40 µg of chromium,
  10 mg of vitamin E,
  100 µg of vitamin B9,
  2.5 µg of vitamin D,
  270 mg of omega-3 fatty acids of plant origin,
  Enough to produce 4.2 g of leucine,
  Enough to produce 0.8 g of tryptophan,
  Enough to produce 0.9 g of arginine,
  Enough to produce 0.75 g of milk calcium, and
  Enough to produce 0.36 g of magnesium.

"Enough to produce Xg" of an element of the composition is defined as the total quantity of this element in the composition: quantity provided by the protides (calcium caseinate, whey isolate, whey concentrate, whey hydrolyzate) and completed by an addition of the element in free form for reaching Xg.

The invention is now illustrated by a study showing the effect of the composition in the reduction of visceral fat on other bariatric operative risk factors.

The study was done on patients:
  Having an excessive waistline circumference relative to the IDF 2006 standards (80 cm for women and 94 cm for men),
  Having at least two cardiometabolic risk factors selected from among: high arterial pressure, high blood sugar, dyslipidemia (high triglycerides, high LDL cholesterol, and high total cholesterol, low HDL), smoking, and family medical history.

The patients followed a regimen adapted to their dietary habits, balanced (50% carbohydrates, 35% lipids, 15% proteins; carbohydrates with a glycemic load of less than 10), hypocaloric (restriction of 700 kcal on the calculated Total Energy Expenditure [TEE]) and comprising two servings per day of a composition according to the invention (that of the example) providing 360 kcal taken into account in the daily ration. A physical activity with a minimum of 5,000 steps (measured with a pedometer) was prescribed. This intensive phase should be stopped when a reduction of 10% of the waistline circumference was reached or when the latter returned to the IDF standards. It should be interrupted at the end of 9 months if the objective has not been reached.

This intensive phase should be followed by a stabilization phase comprising a balanced diet without caloric restriction with one dose of composition according to the invention (that of the example) per day.

92 patients were included in the initial study: contact was lost with 28 of them after the inclusion, 64 completed the intensive nutritional intervention phase, and 34 participated in the stabilization phase.

The basic data of the 64 patients who were included and who completed the intensive nutritional phase of the study are presented in the following table:

TABLE 1

| | Patients Having Completed the Nutritional Intervention Phase (Mean ± Standard Deviation or Number of Patients) N = 64 | |
|---|---|---|
| | Men 15 | Women 49 |
| Mean Age (Years) | 53.7 ± 11.1 | 53.0 ± 11.0 |
| Waistline Circumference (cm) | 101.9 ± 7.3 | 91.9 ± 10.2 |
| Waistline (cm) | 177.8 ± 4.9 | 163.6 ± 6.1 |
| Initial Weight (kg) | 92.3 ± 8.6 | 74.3 ± 11.5 |
| BMI (kg/m$^2$) | 29.2 ± 2.6 | 27.8 ± 4.9 |
| Inclusion of Waistline Circumference Outside the Norms with | | |
| BMI < 25 | 0 | 13 |
| With BMI > 25 | 36 | 15 |
| Including the Obese (BMI > 30) | 4 | 11 |
| REE Basic Metabolism (Kcal) | 1,745 ± 272 | 1,367 ± 110 |
| Body Fat (kg) | 27.6 ± 7.4 | |
| Lean Body Mass (kg) | 50.9 ± 10.0 | |

The results that are obtained for the 64 patients who completed the intensive nutritional phase are presented in the table below:

TABLE 2

| | Initial Value (Mean ± Standard Deviation) | Final Value | Evolution (Mean ± Standard Deviation) | % Evolution |
|---|---|---|---|---|
| REE (Kcal) | 1,455 ± 227 | 1,439.5 ± 201.5 | −15.8 ± 117 | −0.6 |
| Waistline Circumference (cm) | 94.2 ± 10.5 | 85.0 ± 7.5 | −9.2 ± 6.8 | −9.4 |
| Weight (kg) | 78.5 ± 13.3 | 69.3 ± 10.6 | −9.2 ± 5.3 | −11.4 |
| BMI | 28.2 ± 4.5 | 24.8 ± 3.0 | −3.3 ± 2.1 | −11.4 |
| Body Fat (kg) | 27.6 ± 7.4 | 20.0 ± 4.9 | −7.5 ± 6.2 | −25.8 |
| Lean Body Mass (kg) | 50.9 ± 10.0 | 49.3 ± 9.9 | −1.6 ± 3.2 | −3.1 |
| Systolic Arterial Tension (mm of Hg) | 128 ± 15.8 | 117.6 ± 12.1 | −10.5 ± 14.1 | −7.4 |
| Diastolic Arterial Tension (mm of Hg) | 80.2 ± 10.8 | 70.0 ± 6.1 | −10.3 ± 9.7 | −11.7 |
| Total Cholesterol (mmol/l) | 5.7 ± 1.0 | 5.1 ± 0.7 | −0.6 ± 0.6 | −9.4 |
| HDL (mmol/l) | 1.5 ± 0.5 | 1.5 ± 0.4 | 0 ± 0.1 | 0.7 |
| LDL (mmol/l) | 3.6 ± 0.9 | 3.3 ± 0.8 | −0.3 ± 0.5 | −7.9 |
| CT/HDL | 4.2 ± 2.4 | 3.6 ± 1.8 | −0.5 ± 0.8 | −9.4 |
| Triglycerides (mmol/l) | 1.2 ± 1.0 | 1.0 ± 0.3 | −0.2 ± 0.8 | −7.5 |
| Blood Sugar (mmol/l) | 5.8 ± 2.8 | 5.1 ± 0.4 | −0.7 ± 2.7 | −4.8 |
| Insulinemia (μU/ml) | 10.5 ± 6.9 | 7.0 ± 4.6 | −3.5 ± 3.1 | −30.1 |
| HOMA-IR | 3.2 ± 3.8 | 1.6 ± 1.1 | −1.6 ± 3.2 | −35 |
| CRP us (mg/l) | 2.3 ± 3.1 | 1.4 ± 1.6 | −0.9 ± 2.1 | −17.8 |
| Fibrinogen (g/l) | 3.6 ± 0.8 | 3.2 ± 0.6 | −0.5 ± 0.5 | −11.5 |
| Creatinine (mg/l) | 7.8 ± 1.8 | 7.6 ± 1.2 | −0.2 ± 1.2 | / |
| Urea (g/l) | 0.4 ± 0.1 | 0.4 ± 0.4 | 0 ± 0.4 | / |

These results show a weight loss of more than 11%. The number of patients with BMI<25 went from 13 to 41 inclusive at the end of the study. The loss of body fat relative to the lean body mass predominated, bringing the ratio of the lean body mass to the total weight from 65% to 71%.

A mean loss of nearly 10% of the waistline circumference is also noted.

In addition, the composition according to the invention makes possible a significant reduction of other factors of the bariatric operative risk, in particular:

Arterial pressure: arterial pressure is improved. It was normalized in all 17 patients suffering from hypertension, inclusive.

Biological parameters: the biological parameters have been improved, in particular:
  The lipid profile: 11 patients out of 19 normalized their LDL at the end of the weight loss phase
  Inflammation markers: 10 patients who had a high CPR us normalized it as well as 4 patients for fibrinogen, which is unusual
  Insulin resistance markers: 10 patients for blood sugar and 4 patients for insulinemia who were outside the norms regulated the risk of diabetes; in addition, for all of the subjects, a drop of 35% in insulin resistance characterized by HOMA-IR3 was noted Creatinine was lowered, and urea remained stable, which suggests that the nutritional protocol used in the study does not have a detectable impact on renal function.

The reduction of 10% of the waistline circumference brings about a reduction in the size of the liver due to the loss of hepatocytic body fat. This makes possible better accessibility of the stomach for the surgeon but primarily perfectly prepares the patient by eliminating shortcomings that could cause post-operative problems such as poor healing or edema.

In addition, the loss of visceral fat before the operation brings about a larger loss one year after the intervention.

Furthermore, advantageously, in 6 months, no undesirable effect was reported spontaneously.

The invention claimed is:

1. A dietary composition, comprising:
   A whey hydrolyzate with a molecular weight of between 200 and 10,000 daltons,
   An isolate and/or a concentrate of whey, and
   Calcium caseinate,
   wherein the composition comprises:
   1.5% to 3% tryptophan,
   12% to 20% branched amino acids,
   6% to 10% aromatic amino acids,
   0.8% to 1.5% taurine,
   1.6% to 3% arginine,
   1.2% to 3% milk calcium,
   0.5% to 1% magnesium,
   0.4% to 1% omega-3 fatty acids,
   1 to 2 mg of vitamin B6 per 50 g of the composition without vehicles,
   5 to 15 mg of zinc per 50 g of composition without vehicles,
   1 to 3 µg of vitamin D per 50 g of composition without vehicles,
   75 to 150 µg of chromium per 50 g of composition without vehicles,
   100 µg of vitamin B9 per 50 g of composition without vehicles,
   10 mg of vitamin E per 50 g of composition without vehicles, and
   said percentages being given by weight of dry material of all of the active ingredients that are present in the composition.

2. The composition according to claim 1, wherein the isolate and/or the concentrate has/have a molecular weight of between 15,000 and 20,000 daltons.

3. The composition according to claim 1, wherein the calcium caseinate has a molecular weight of between 20,000 and 35,000 daltons.

4. The composition according to claim 1, wherein the whey hydrolyzate has a molecular weight of between 200 and 3,500 daltons.

5. The composition according to claim 1, wherein the ratio by weight between calcium caseinate and the total of the whey hydrolyzate and the isolate and/or the concentrate of whey is between 0.8 and 1.2.

6. The composition according to claim 1, wherein the mixture of active ingredients further comprises a mixture of amino acids.

7. The composition according to claim 6, wherein the mixture of amino acids comprises at least one of tryptophan, glutamine, leucine, arginine, and taurine.

8. The composition according to claim 7, wherein tryptophan represents between 6% and 9% by weight of the neutral amino acids that are present in the composition.

9. The composition according to claim 7, wherein the ratio of the weight of arginine to the weight of taurine is between 1.5 and 2.

10. The composition according to claim 1, wherein
    the whey hydrolyzate represents between 8% and 12%,
    the isolate and/or the concentrate of whey represents between 15% and 20%, and
    calcium caseinate represents between 20% and 25%, of the composition,
    with the percentages being given by weight of dry material of all of the active ingredients that are present in the composition.

11. The composition according to claim 1, in the form of powder or granules, ready-to-use drink, food bars or logs.

12. A method of reducing visceral fat in an obese individual during the pre-operative phase of a bariatric surgery intervention, comprising orally administering to said obese individual, a diet composition comprising:
    A whey hydrolyzate with a molecular weight of between 200 and 10,000 daltons,
    An isolate and/or a concentrate of whey, and
    Calcium caseinate
    wherein the composition comprises:
    1.5% to 3% tryptophan,
    12% to 20% branched amino acids,
    6% to 10% aromatic amino acids,
    0.8% to 1.5% taurine,
    1.6% to 3% arginine,
    1.2% to 3% milk calcium,
    0.5% to 1% magnesium,
    0.4% to 1% omega-3 fatty acids,
    1 to 2 mg of vitamin B6 per 50 g of the composition without vehicles,
    5 to 15 mg of zinc per 50 g of composition without vehicles,
    1 to 3 µg of vitamin D per 50 g of composition without vehicles,
    75 to 150 µg of chromium per 50 g of composition without vehicles,
    100 µg of vitamin B9 per 50 g of composition without vehicles, and
    10 mg of vitamin E per 50 g of composition without vehicles,
    said percentages being given by weight of dry material of all of the active ingredients that are present in the composition.

13. The method according to claim 12, wherein the isolate and/or the concentrate has/have a molecular weight of between 15,000 and 20,000 daltons.

14. The method according to claim 12, wherein the calcium caseinate has a molecular weight of between 20,000 and 35,000 daltons.

15. The method according to claim 12, wherein the ratio by weight between calcium caseinate and the mixture consisting of the hydrolyzate and the isolate and/or the concentrate of whey is between 0.8 and 1.2.

* * * * *